United States Patent [19]

Flora

[11] Patent Number: 4,822,609
[45] Date of Patent: Apr. 18, 1989

[54] TREATMENT OF OSTEOPOROSIS

[75] Inventor: Lawrence Flora, Fairfield, Ohio

[73] Assignee: The Procter & Gamble Company, Cincinnati, Ohio

[21] Appl. No.: 906,725

[22] Filed: Sep. 12, 1986

Related U.S. Application Data

[63] Continuation of Ser. No. 684,542, Dec. 21, 1984, abandoned, which is a continuation-in-part of Ser. No. 605,541, Apr. 30, 1984, abandoned.

[51] Int. Cl.$^4$ ...................... A61K 31/66; A61K 35/55
[52] U.S. Cl. .................................... 424/112; 424/128; 424/151; 514/141; 514/167
[58] Field of Search ................ 424/112, 128; 514/167, 514/141

[56] References Cited

U.S. PATENT DOCUMENTS

| 3,683,080 | 8/1972 | Francis | 424/204 |
| 4,230,700 | 10/1980 | Francis | 424/204 |
| 4,330,537 | 5/1982 | Francis | 424/204 |

FOREIGN PATENT DOCUMENTS 110294 6/1984 European Pat. Off.
3243358 5/1984 Fed. Rep. of Germany.

OTHER PUBLICATIONS

Anderson et al., "Preliminary Observations of a Form of Coherence Therapy for Osteoporosis", *Calcif. Tissue Int.*, vol. 36 (1984), pp. 341-343.

Frost, "*Editorial*-The ADFR Concept Revisited", *Calcif. Tissue Int.*, vol. 36 (1984), pp. 349-353.

Hodsman et al., "Clinical Studies of Patients Currently Enrolled in Cyclical (ADFR) Therapy for Osteoporosis", Abstract from Feb. 1984, Meeting in London Ont. Copy of Slide "Coherence Therapy Trial", Projected on a Screen During Dr. Anderson's Talk at the Sun Valley Meeting, Aug. 1983.

Recker, "Stimulation of New Bone Formation by the 'ADFR' Technique in Dogs", in *Bone Histomorphometry 1980*, (Jee and Parifitt Editors), Armour-Montagu, Levallois (1981), pp. 331-336.

Chesnut, "Synthetic Salmon Calcitonin, Diphosphonates, and Anabolic Steroids in the Treatment of Postmenopausal Osteoporosis", Osteoporosis-Proceedings of the Copenhagen International Symposium on Osteoporosis Jun. 3-8, 1984, (Christiansen et al., Editors), Aalborg Stiftsbogtrykkeri (1984), pp. 549-555, see pp. 551-552.

Adami et al., "Dichloromethylene-Diphosphonate Therapy of Osteolytic Lesions and Osteoporosis", Osteoporosis-Proceedings of the Copenhagen International Symposium on Osteoporosis Jun. 3-8, 1984, (Christiansen et al., Editors), Aalborg Stiftsbogtrykkeri (1984), pp. 643-645.

Reeve et al., "Studies of a 'Short-Cycle' ADFR Regime Using Parathyroid Peptide hPTH 1-34 in Idiopathic Osteoporosis and in a Dog Model", Osteoporosis-Proceedings of the Copenhagen International Symposium on Osteoporosis Jun. 3-8, 1984, (Christiansen et al., Editors), Aalborg Stiftsbogtrykkeri (1984) pp. 567-573.

Rasmussen et al., "Effect of Combined Therapy with Phosphate and Calcitonin on Bone Volume in Osteoporosis", *Metab. Bone Dis. & Rel. Res.*, vol. 2 (1980) pp. 107-111.

Rasmussen, "Considerations as to the Pathogenesis and Treatment of Osteoporosis", in *Bone Histomorphometry 1980*, (Jee and Parifitt Editors), Armour-Montagu, Levalloi (1981), pp. 311-316.

Marie et al., "Treatment of Postmenopausal Osteoporosis with Phosphate and Intermittent Calcitonin", Osteoporosis-Proceedings of the Copenhagen International Symposium on Osteoporosis Jun. 3-8, 1984, (Christiansen et al., Editors), Aalborg Stiftsbogtrykkeri (1984), pp. 575-579.

Berthel et al., "Treatment of Post Menopausal Osteoporosis with Phosphate and Intermittent Calcitonin:Effect on Cortical Bone", Osteoporosis-Proceedings of the Copenhagen International Symposium on Osteoporosis Jun. 3-8, 1984 (Christiansen et al., Editors), Aalborg Stiftsbogtrykkeri (1984) pp. 651-652.

Ortolani et al., "Treatment of Postmenopausal and Senile Osteoporosis with Combined Calcitonin and 1.25-Dihydroxycholecalciferol", Osteoporosis–Proceedings of the Copenhagen International Symposium on Osteoporosis Jun. 3-8, 1984, Christiansen et al., Editors), Aalborg Stiftsbogtrykkeri (1984), pp. 625-628.

Geusens and Dequeker, "Effect of Anabolic Steroids, 1-Alpha Hydroxyvitamin D and Intermittent Calcium Infusions on Bone Mineral Content in Osteoporosis", Osteoporosis-Proceedings of the Copenhagen International Symposium on Osteoporosis, Jun. 3-8, 1984, (Christiansen et al., Editors), Aalborg Stiftsbogtrykkeri (1984) pp. 665-667.

Delmas et al., "Cyclic Fluoride Therapy for Postmenopausal Osteoporosis", Osteoporosis-Proceedings of the Copenhagen International Symposium on Osteoporosis Jun. 3-8, 1984, (Christiansen et al., Editors), Aalborg Stiftsbogtrykkeri (1984) pp. 581-586.

Meunier et al., "Treatment of Primary Osteoporosis with Drugs that Increase Bone Formation:Sodium Flu- (List continued on next page.)

*Primary Examiner*—Leonard Schenkman
*Attorney, Agent, or Firm*—Milton B. Graff, IV; Steven J. Goldstein; Jack D. Schaeffer

[57] ABSTRACT

A method for treating or preventing osteoporosis is disclosed. Bone cells are synchronized during a bone cell activating period; bone resorption, which normally follows activation, is inhibited using a polyphosphonate; bone formation is allowed to occur in the rest period during which nutrient supplements may be administered to the patient. The method shortens the natural cycle time of bone formation/resorption, resulting in a faster bone build-up.

16 Claims, No Drawings

OTHER PUBLICATIONS oride, hPTH1-34, ADFR Concept", Osteoporosis--Proceedings of the Copenhagen International Symposium on Osteoporosis Jun. 3-8, 1984, (Christiansen et al., Editors), Aalborg Stiftsbogtrykkeri (1984) pp. 595-602.

Kleerekoper et al., "Treatment of Osteoporosis with Sodium Fluoride Alternating with Calcium and Vitamin D", Osteoporosis:Recent Advances in Pathogenesis and Treatment, (DeLuca et al., Editors), University Park Press, Baltimore, MD (1981) pp. 441-448.

Briancon and Meunier, "Treatment of Osteoporosis with Fluoride, Calcium, and Vitamin D", *Orthop. Clin. N. Amer.*, vol. 12 (1981), pp. 629-648.

Siris et al., "Long-Term Therapy of Paget's Disease of Bone with EHDP", *Arthritis and Rheumatism*, 23(10), pp. 1177-1184 (1980).

Meunier et al., "Effects of Disodium Dichloromethylene Diphosphonate on Paget's Disease of Bone", *Adv. Exp. Med. Biol.*, 128, pp. 299-309 (1980).

Bonjour et al., "Action of 1,25-Dihydroxyvitamin $D_3$ and a Diphosphonate on Calcium Metabolism in Rats", *Amer. J. Physiology*, vol. 229 (1975), pp. 402-408.

Bonjour et al., "Influence of 1,25-Dihydroxycholecalciferol and Diphosphonate on Calcium Metabolism", *Experientia*, vol. 29(1973), p. 740.

Boris et al., "Evidence for the Promotion of Bone Mineralization by 1-Alpha, 25-Dihydroxycholecalciferol in the Rat Unrelated to the Correction of Deficiencies in Serum Calcium and Phosphorus", J. Nutr., vol. 108 (1978), pp. 1899-1906.

Mallon, et al., "Effect of Diphosphonates on Bone Mineralization and Serum Levels of 1-Alpha, 25-Dihydroxyvitamin D in Rats", *Proceedings of the Workshop on Vitamin D*, 1982, 809-811 (1982).

Mallon, et al., "Effect of Diphosphonates on Bone Mineralization and Serum Levels of 1-Alpha, 25-Dihydroxyvitamin D in Rats", Abstract from the Fifth Workshop on Vitamin D, Historic Williamsburg, Virginia, Feb. 14-19, 1982.

Frost, "Treatment of Osteoporoses by Manipulation of Coherent Bone Cell Population", *Clin. Orth. Rel. Res.*, vol. 143(1979), pp. 227-244.

Frost, "The ADFR Concept and Monitoring It", in *Bone Histomorphometry* 1980, (Jee and Parifitt, Editors), Armour-Montagu, Levallois (1981), pp. 317-321.

Frost, "The Evolution of Osteoporosis Therapy", Orthop. Clin. N. Amer. vol. 12, (1981), pp. 603-610.

Frost, "Coherence Treatment of Osteoporoses", *Orthop. Clin. N. Amer.*, vol. 12 (1981), pp. 649-669.

Frost, "Clinical Management of the Symptomatic Osteoporotic Patient", *Orthop. Clin. N. Amer.*, vol. 12 (1981), pp. 671-681.

Frost, "Osteoporoses:Quo Vadis!", *Orthop. Clin. N. Amer.*, vol. 12 (1981), pp. 683-691.

Frost, "Review Article—The Skeletal Intermediary Organization", *Metab. Bone Dis. & Rel. Res.*, vol. 4 (1983), pp. 281-290.

Francis and Martodam, "Ch. 4-Chemical, Biochemical, and Medicinal Properties of the Diphosphonates", in *The Role of Phosphonates in Living Systems*, (Hildebrand, Editor), CRC Press, Inc., Boca Raton, Fla. (1983), pp. 55-96.

Recker, "Continuous Treatment of Osteoporosis:Current Status", *Orthop. Clin. N. Amer.*, vol. 12 (1981), pp. 611-627.

Hesch, et al.; *Acta Endocr. (Kobenhavn)*, 108 (267, suppl), pp. 171-172 (1985).

TREATMENT OF OSTEOPOROSIS

CROSS REFERENCE TO RELATED APPLICATIONS

This is a continuation of application Ser. No. 684,542, filed Dec. 21, 1984, which is a continuation-in-part of application Ser. No. 605,541, filed Apr. 30, 1984, both abandoned.

TECHNICAL FIELD

The present invention relates to a method for the treatment or prevention of osteoporosis. Specifically, the present invention relates to a method whereby a bone cell activating compound and a bone resorption inhibiting polyphosphonate are sequentially administered to a subject afflicted with or at risk to osteoporosis.

Osteoporosis is the most common form of metabolic bone disease. Although it may occur secondary to a number of underlying diseases, 90% of all cases appear to be idiopathic.

Idiopathic osteoporosis is most commonly observed in postmenopausal women (postmenopausal osteoporosis) but is may also occur in elderly males and females (senile osteoporosis) or occasionally in younger individuals of both sexes. The disease which develops in post-menopausal women is characterized primarily by fractures of the wrist and spine, while femoral fractures seem to be the dominant feature of senile osteoporosis.

The fractures which occur in the various forms of osteoporosis are caused primarily by a gradual loss of bone which eventually reaches the point of mechanical failure. The physical nature of the bone which remains also seems to be compromised but the role which this plays in the loss of bone strength is unclear.

The mechanism by which bone is lost in osteoporotics is believed to involve the process by which the skeleton renews itself. This process has been termed bone remodeling. It occurs in a series of discrete pockets of activity. These pockets appear spontaneously within the bone matrix on a given bone surface as a site of bone resorption. There is apparently an activation of percursor cells within these pockets to form osetoclasts (bone dissolving or resorbing cells) which, in turn, resorb a portion of bone of generally constant dimensions. This process is followed by the appearance of osteoblasts (bone forming cells) which then refill the cavity left by the osteoclasts with new bone.

In a healthy adult subject, the rate at which osteoclasts and osteoblasts are formed is such that bone formation and bone resorption are in balance. However, in osteoporotics an imbalance in the bone remodeling process develops which allows bone to be lost at a rate faster than it is being made. Although this imbalance occurs to some extent in most individuals as they age, it is much more severe and occurs at a younger age in osteoporotics, particularly those who develop the post-menopausal form of the condition.

There have been many attempts to treat osteoporosis with a variety of pharmacologic agents with the goal being to either slow further bone loss or to produce a net gain in bone mass. It appears as though there are agents available which will slow further bone loss in osteoporotics but agents or methods of treatment which will result in the replacement of bone which has already been lost have been very elusive. The reason for this probably lies in the tight coupling characteristics of bone remodeling. Agents or methods of treatment which stimulate or suppess one phase of the cycle (either resorption or formation) tend to have a similar effect on the opposing process. Therefore most attempts to treat osteoporosis have resulted in no more than a transient change and when the opposing process is stimulated or suppressed, the change is then negated.

Using a different approach, it has been attempted to induce bone activation by continuous administration of inorganic phosphate and to separately inhibit bone resorption by intermittent administration of calcitonin. This method has been shown to result in net bone formation in patients with post-menopausal osteoporosis. Furthermore, a theoretical model has been proposed which suggests that it may be possible to synchronize bone cell activity and metabolism by administering bone activating agents. Once synchronized, it should then be possible to limit the resorption by administering a bone resorption inhibiting agent during the natural life of the resorption phase of the bone remodeling unit. The model does not address the problem of bone formation inhibition which is typically associated with the administration of a bone resorption inhibiting agent. Furthermore, it is desirable to shorten the natural cycle of bone resorption/formation, in order to achieve faster overall bone build up.

It is therefore an object of the present invention to provide a method for treating osteoporosis which does not require a prolonged administration of pharmacologic agents, and which does not result in a significant inhibition of bone formation. It is a further object of this invention to provide a method which shortens the natural cycle time of bone formation/resorption.

BACKGROUND OF THE INVENTION

U.S. Pat. No. 4,230,700, issued Oct. 28, 1980 to Francis, discloses the conjoint administration of certain polyphosphonate compounds, in particular diphosphonates, and vitamin D-like anti-rachitic compounds for inhibition of the anomalous mobilization of calcium phosphates in animal tissue. U.S. Pat. No. 4,330,537, issued May 18, 1982 to Francis, claims the compositions used in the methods of U.S. Pat. No. 4,230,700. The patents specify that the administration of the phosphonate and the vitamin D-like compound be conjoint; moreover, the vitamin D-like compounds (unlike certain vitamin D metabolities) do not qualify as bone cell activating compounds.

Rasmussen et al., "Effect of Combined Therapy with Phosphate and Calcitonin on Bone Volume in Osteoporosis", *Metabolic Bone Disease and Related Reseach*, 2, 107 (1980), discloses a treatment regimen consisting of continuous administration of inorganic phosphate and intermittent administration of calcitonin. A net bone formation was observed.

Frost, "Treatment of Osteoporosis by Manipulation of Coherent Bone Cell Populations", *Clinical Orthopedics and Related Research*, 143, 227 (1979), discloses a theoretical model which suggests that it should be possible to synchronize the activity and metabolism of bone cells by administering bone cell activating agents. Once the cells have been synchronized, their resorption activity could be effectively inhibited by administration of a bone resorption inhibiting agent. The model requires that the bone resorption inhibiting agent be administered throughout the bone resorption phase of the bone remodeling unit. Furthermore, the model suggests that administration of a high does of the bone resorption inhibiting agent is desirable because the bone resorption should be inhibited as much as possible. The model assumes that bone formation inhibition does not take place, because no bone resorption inhibiting agent is administered during the bone formation phase of the bone remodeling unit.

SUMMARY OF THE INVENTION

The present invention relates to a method for treating or preventing osteoporosis in humans or lower warm blooded animals comprising administering to a subject afflicted with or at risk to osteoporosis a bone cell activating compound and a bone resorption inhibiting polyphosphonate according to a regimen consisting of two or more cycles, whereby each cycle consists of: (a) a bone activating period of from about 1 day to about 5 days, preferably about 3 days, during which a bone activating amount of a bone cell activating compound is administered daily to said subject; followed by (b) a bone resorption inhibition period of from about 10 days to about 20 days, preferably about 14 days, during which a bone resorption inhibiting polyphosphonate is administered daily to said subject in an amount of from about $0.25 \times LED$ to about $3.3 \times LED$; followed by (c) a rest period of from about 30 days to about 60 days, preferably from about 40 to about 50 days, during which the subject receives neither bone cell activating compound nor a bone resorption inhibiting polyphosphonate.

DETAILED DESCRIPTION OF THE INVENTION

The treatment regimen of the present invention consists of one or more cycles, whereby each cycle consists of a bone activating period, a bone resorption inhibition period and a rest period. During the bone activating period, bone cells are induced into a synchronized metabolism. During the bone resorption inhibition period, the bone resorption which naturally follows the activation is limited to a minimum by administration of a bone resorption inhibiting polyphosphonate. The rest period allows for natural bone formation to occur.

The preferred mode of administration is orally, but other modes of administration include, without limitation, intramuscular, intravenous, intraperitoneal, and subcutaneous administration, as well as topical application. All compounds described herein are administered orally, except where specified otherwise.

By "subject afflicted with or at risk to osteoporosis" as used herein is meant a subject diagnosed as suffering from one or more of the various forms of osteoporosis, or a subject belonging to a group known to have a significantly higher than average chance of developing osteoporosis, e.g., post-menopausal women, men over the age of 65, and persons being treated with drugs known to cause osteoporosis as a side effect (such a adrenocorticoid).

By "bone cell activating compound" as used herein is meant a compound which increases the rate of activation of new remodeling units on bone. The concept is described in more detail in Frost, *Clinical Orthopedics and Related Research*, 143, 227 (1979) and in Rasmussen et al., *Metabolic Bone Disease and Related Research*, 2, 107 (1980), the disclosures of which are incorporated herein by reference. In most cases this increased rate of activation is initially manifested by an increase in the number of bone resorbing cells and bone resorbing sites. Biochemical indicies of skeletal remodeling, such as urinary hydroxyproline levels, are expected to become elevated according to the magnitude of the response to the bone cell activating compound. Specific examples of such compounds are parathyroid hormone (PTH), inorganic phosphate, growth hormone, fluoride, thyroid hormones (e.g. thyroxine), certain vitamin D metabolites and prostaglandins. It may be possible to induce bone cell activation by non-chemical means, e.g. a strict, physical exercise regimen, or electrical currents.

By "bone cell activating amount" as used herein is meant an amount of the bone cell activating agent sufficient to effect a medically significant increase of the rate of activation of new remodeling units. If inorganic phosphate is used as the bone cell activating compound, the amount is in the range of from about 4 mg/kg/day (P.O.) to about 60 mg/kg/day (P.O.) of phosphorus, with amounts of from about 30 mg P/kg/day to about 50 mg P/kg/day preferred. Daily doses of inorganic phosphate should not exceed about 3.6 grams of phosphorous for any subject afflicted with or at risk to osteoporosis because severe diarrhea and gastrointestinal distress is likely to occur for dosages which exceed this amount.

Bone cell activating amounts of other bone cell activating compounds are as follows: 1,25-dihydroxy vitamin $D_3$ and other 1-hydroxy vitamin D metabolites: from about 0.001 microgram/kg/day to about 0.03 microgram/kg/day (P.O.); 25-hydroxy vitamin $D_3$ and other 25-hydroxy vitamin D metabolites (not including 1,25-dihydroxy vitamin D metabolites): from about 0.1 microgram/kg/day to about 3 microgram/kg/day (P.O.); inorganic fluoride (e.g. sodium fluoride): from about 0.1 mg/kg/day to about 1.0 mg/kg/day F per day (P.O.); thyroxine: from about 0.01 mg/kg/day to about 0.5 mg/kg/day (P.O.); triiodothyroxine: from about 0.1 microgram/kg/day to about 2.5 microgram/kg/day per day (P.O.); prostaglandin $PGE_2$: from about 0.1 to about 25 mg/kg/day (P.O.); parathyroid hormone 1-34: from about 0.1 microgram/kg/day to about 3.0 microgram/kg/day (S.C.).

By "bone resorption inhibiting polyphosphonate" as used herein is meant a polyphosphonate of the type disclosed in U.S. Pat. No. 3,683,080, granted Aug. 8, 1972, Francis, the disclosures of which are incorporated herein by reference. The term "phosphonate" includes the phosphonic acids, as well as their pharmaceutically acceptable salts and esters. Preferred polyphosphonates are geminal diphosphonates (also referred to as bisphosphonates or diphosphonates). The polyphosphonates may be administered in the form of the acid, or of a soluble alkali metal salt or alkaline earth metal salt. Hydrolyzable esters of the polyphosphonates are likewise included. Specific examples include ethane-1-hydroxy-1,1-diphosphonic acid, pentane-1-hydroxy-1,1-diphosphonic acid methane diphosphonic acid, methane dichloro diphosphonic acid, methane hydroxy diphosphonic acid, ethane-1-amino-1,1-diphosphonic acid, ethane-2-amino-1,1-diphosphonic acid, propane-3-amino-1-hydroxy-1,1-diphosphonic acid, propane-N,N-dimethyl-3-amino-1-hydroxy-1,1-diphosphonic acid, propane-3,3-dimethyl-3-amino-1-hydroxy-1,1-diphosphonic acid, phenyl amino methane diphosphonic acid, N,N-dimethylamino methane diphosphonic acid, N(2-hydroxyethyl) amino methane diphosphonic acid, butane-4-amino-1-hydroxy-1,1-diphosphonic acid, pentane-5-amino-1-hydroxy-1,1-diphosphonic acid, hexane-6-amino-1-hydroxy-1,1,-diphosphonic acid, and pharmaceutically acceptable esters and salts thereof.

The amount of the polyphosphonate to be used is determined entirely by its potency as a bone resorption inhibiting agent. This potency is determined by means of the thyroparathyroidectomized (TPTX) rat model described herein and expressed as the lowest effective dose (LED) of the compound which is defined as the lowest subcutaneously given dose of polyphosphonate, in mg P per kg body weight, which in the TPTX rat model results in an inhibiton of the PTH-induced rise in serum calcium level. Since the amount of polyphosphonate to be administered is dependent on the bone resorption inhibition potency of the compound, the amount to be administered is conveniently expressed as multiples of LED. Extrapolation of the dosages for polyphosphonates from the TPTX rat model to humans is possible based on the observation that oral dosages in humans are proportionally related to the LEDs for polyphosphonates in the TPTX rat model. It is therefore observed that suitable amounts of polyphosphonates for administration in subjects afflicted with or at risk to osteoporosis are from about 0.25×LED to about 3.3×LED, while amounts of from about 0.25×LED to about 2.5×LED are preferred, and amounts of from 0.50×LED to 2.0×LED are most preferred. The LEDs of a number of polyphosphonates are collected in Table I.

Ranges for the daily administration of some polyphosphonates for subjects afflicted with or at risk to osteoporosis are therefore: ethane-1-hydroxy-1,1-diphosphonic acid: from about 0.25 mg P/kg to about 3.3 mg P/kg, with from about 0.25 mg P/kg to about 2.5 mg P/kg preferred; dichloromethane diphosphonic acid: from about 0.12 mg P/kg to about 1.67 mg P/kg, with from about 0.12 mg P/kg to about 1.25 mg P/kg preferred; propane-3-amino-1-hydroxy-1,1-diphosphonic acid: from about 0.025 mg P/kg to about 0.33 mg P/kg, with from about 0.025 mg P/kg to about 0.25 mg P/kg preferred; butane-4-amino-1-hydroxy-1,1-diphosphonic acid: from about 0.0025 mg P/kg to about 0.033 mg P/kg, with from about 0.0025 mg P/kg to about 0.025 mg P/kg preferred; and hexane-6-amino-1-hydroxy-1,1-diphosphonic acid: from about 0.025 mg P/kg to about 0.33 mg P/kg, with from about 0.025 mg P/kg to about 0.25 mg P/kg preferred.

An important aspect of the present invention is the discovery that too high a dosage of polyphosphonate is detrimental to net bone formation. In fact, dosages which are routinely prescribed for the treatment of Paget's disease appear on the high side for treatment in the present regimen. Generally, polyphosphonate dosage should not exceed about 3.3×LED/day, and are preferably below about 2.5×LED/day. Polyphosphonate dosage below 2.0×LED/day are most preferred.

Another important aspect of the present invention is the discovery that the natural cycle time of bone resorption/formation can be shortened. As disclosed in Frost, "Treatment of Osteoporosis by Manipulation of Coherent Bone Cell Populations," *Clinical Orthopedics and Related Research*, 143, 227 (1979), the disclosures of which are incorporated herein by reference, the natural cycle time varies from 3 to 6 months. With the method of the present invention it is possible to reduce the cycle time to about 41 to about 85 days. Thus, it is possible to repeat the treatment cycle up to 9 times a year, as distinguished from 2-4 times a year based on the natural cycle. The shorter cycle time is believed to result in a faster overall bone build-up.

Neither bone cell activating compounds nor bone resorption inhibiting polyphosphonate are administered during the rest period. This is not to say that no chemical should be administered to the patient at all during this period. Food supplements like calcium and vitamin D (to be distinguished from bone cell activating metabolites of vitamin D) can beneficially be administered during this period.

Thyroparathyroidectomized (TPTX) Rat Model

To determine the bone resorption inhibition potency of several polyphosphonates, the following animal model was used.

In this study 50 male Wistar rats weighing approximately 150-160 grams were thyroparathyroidectomized surgically by the breeder (Charles River Breeding Laboratories ®). All rats were double housed on arrival in suspended cages with Purina Laboratory Rodent Chow ® and tap water ad libitum. After acclimation to the laboratory environment for 3–5 days, the rats were placed on a low calcium, low phophorous (0.18%/0.22%) diet (Teklad ®) and given 2% (W/V) calcium gluconate supplemented deionized water via water bottles.

On day four of low-calcium diet all rats were anesthetized with Ketaset ® (Ketamine Hydrochloride, 100 mg/ml, Bristol Myers), 0.10 ml/100 grams of body weight, weighed and then bled for serum total calcium analysis using Flame Atomic Absorption (FAA). All rats weighing less than 180 grams were eliminated from the study. Animals were then randomized statistically such that the mean total calcium for each group was the same. Only rats deemed hypocalcemic (total calcium ≦ 8.0 mg/dl) were placed in study groups (6 animals in each group).

Treatments with the various experimental compounds commenced on day 6 and lasted through day 9 of the study (at 1:00 P.M. each day). Dose solutions were prepared to be given at a constant rate of 0.2 ml/100 grams of body weight subcutaneously in the skin flap where the hind leg meets the torso. All rats were weighed and dosed daily. A 25 gauge ⅝" needle was used to administer drug, alternating dose sites daily. On day 9 all rats were fasted in the afternoon at approximately 4:00 P.M. On day 10 of study no treatment was given. In the morning a 600 μl sample of whole blood was collected from each rat in Microtainer (B-D#5060) serum separater tubes for serum total calcium (FAA).

Two 125 μl samples of heparinized whole blood were also collected to be used for ionized calcium analysis. Immediately following blood collection all rats were weighed and injected with bovine parathyroid hormone subcutaneously at a rate of 75 USP units per 100 grams of body weight. Blood sampling for total and ionized calcium was repeated three hours post-PTH injection.

Statistic

All pre- and post-PTH total and ionized calciums were statistically analyzed for significane compared to PTH along (control) using Student's t-test, analysis of variance, and their non-parametric equivalents. The post minus pre-change and % change were also determined on calcium levels and pre-drug vs post-drug body weights.

Materials

Low calcium and phophorous diets used were prepared by Teklad ® Test Diets (Harlan Industries, Madison, Wis. 53711; Order #TD82195) in a pellet form of approximately 0.18% calcium and 0.22% phosphorous. The diets contained all the essential vitamins and minerals required for the rat, with the exception of calcium and phophorous. The calcium and phosphorous levels of the pellets were verified analytically.

All dosing solutions of compounds to be tested for bone resorption inhibition potency were adjusted to pH 7.4 with sodium hydroxide and prepared in 0.9% saline (Abbott NDC 0074-1583-03), Abbott Labs, North Chicago, IL 60064, USA). Dosing solution concentrations were adjusted to a dosing rate of 0.20 ml/100 grams of body weight.

PTH was acquired as a powdered bovine extract (Sigma Chemical Co., P.O. Box 14508, St. Louis, Mo., order #P-0892, Lot #72F-9650) at an activity of 138 USP units per mg. PTH was prepared in 0.9% saline such that the final concentration was 100 U.S.P./ml. All solutions were filtered through a 190 40 Whatman Filter Paper then 0.45 μm Metricel ® filter.

The physiological effect of the PTH challenge is a rise in serum calcium level. Since the animals were on a low calcium diet, an observed increase in serum calcium level is the result of a resorption of bone material. Since polyphosphonates tend to inhibit resorption of bone material, the animals pretreated with polyphosphonate showed a rise in serum calcium level upon PTH challenge which was less than that found in control animals which had been treated with saline vehicle instead. The lowest dose at which the polyphosphonate is capable of inhibiting bone resorption, as evidenced by a decreased rise in serum calcium upon PTH challenge, is a measure of the bone resorption inhibition potency of the polyphosphonate. Where necessary the test was repeated, whereby the animals were administered with 0.5 and 0.2×LED, in order to refine the determination of LED. The LED values of some representative diphosphonates are presented in Table I.

TABLE I

| Lowest Effective (antiresorptive) Dose (LED) Values | |
|---|---|
| Compound* | LED (mg P/kg) |
| ethane-1-hydroxy-1,1-diphosphonic acid (EHDP) | 1.0 |
| dichloromethane diphosphonic acid (Cl$_2$MDP) | 0.5 |
| propane-3-amino-1-hydroxy-1,1-diphosphonic acid (APD) | 0.10 |
| butane-4-amino-1-hydroxy-1,1-diphosphonic acid (ABDP) | 0.01 |
| hexane-6-amino-1-hydroxy-1,1-diphosphonic acid (AHDP) | 0.10 |

*All compounds were in aqueous solution, the pH of which had been adjusted to 7.4 with NaOH. At this pH the diphosphonic acids are present as their disodium salts.

EXAMPLE

Patients clinically diagnosed as suffering from osteoporosis are subjected to a treatment regimen according to the present invention as follows. Each patient is subjected to from 3 to 8 cycles, each cycle consisting of (a) a bone activating period of 3 days during which 2 tablets of Phosphate Sandoz ™ were administered 3 times daily (each tablet contains 500 mg of elemental phosphorous); (b) a bone resorption inhibition period of 14 days during which the patients receive 5 mg/kg/day (corresponding to 1.24 mg P/kg/day, or 1.24×LED) of DIDRONEL (Norwich Eaton Pharmaceuticals, Norwich, N.Y.) divided into 3 doses (each DIDRONEL tablet contains 200 mg of disodium EHDP); (c) a rest period of 45 days during which the patients receive a diet which is verified to contain a minimum of 1 g/day of calcium.

The treatment regimen results in an appreciable alleviation of osteoporotic conditions.

The treatment regimen is varied as indicated in Table II.

TABLE II

| Bone Activating Period | | | Bone Resorption Inhibition Period | | | Rest Period Days | Total Cycle Days |
|---|---|---|---|---|---|---|---|
| Days | Compound | Dose/day | Days | Compound | Dose/day (mg P/kg) | | |
| 1 | 1,25-Vit. D$^{(a)}$ | 1 μg | 10 | Cl$_2$MDP | 2.5 | 30 | 41 |
| 3 | NaF | 20 mg | 12 | APD | 0.5 | 40 | 55 |
| 5 | PTH 1-34$^{(b)}$ | 100 μg | 17 | AHDP | 0.03 | 50 | 72 |
| 3 | PGE$_2$$^{(c)}$ | 10 mg/kg | 15 | ABDP | 0.005 | 60 | 78 |

$^{(a)}$1,25 dihydroxy vitamin D$_3$
$^{(b)}$parathyroid hormone 1-34
$^{(c)}$prostaglandin E$_2$ A treatment regimen consisting of two or more of the above cycles results in an appreciable alleviation of osteoporotic conditions.

What is claimed is:

1. A method for treating or preventing osteoporosis in humans comprising administering to a subject afflicted with or at risk to osteoporosis a bone cell activating compound and a bone resorption inhibiting polyphosphonate according to a regimen consisting of two or more cylces, whereby each cycle consists of: (a) a bone activating period of from about 1 day to about 5 days during which a bone activating amount of a bone cell activating compound is administered daily to said subject; followed by (b) a bone resorption inhibition period of from about 10 days to about 20 days during which ethane-1-hydroxy-1,1-diphosphonic acid, or a pharmaceutically-acceptable salt or ester thereof, is administered daily to said subject in an amount of from about 0.25 mgP/kg/day to about 3.3 mgP/kg/day; followed by (c) a rest period of from about 30 days to about 60 days during which the subject receives neither a bone cell activating compound nor a bone resorption inhibiting polyphosphonate.

2. The method of claim 1 wherein during the bone resorption inhibition period the ethane-1-hydroxy-1,1-diphosphonic acid, or pharmaceutically-acceptable salt or ester thereof, is administered daily in an amount of from about 0.25 mgP/kg/day to about 2.5 mgP/kg/day.

3. The method of claim 1 wherein the rest period is from about 40 days to about 50 days.

4. The method of claim 2 wherein the rest period is from about 40 days to about 50 days.

5. The method of claim 2 wherein the bone cell activating compound is an inorganic phosphate and the bone activating amount is from about 4 mg/kg/day to about 60 mg/kg/day of phosphorous, and not to exceed about 3600 mg P/day.

6. The method of claim 5 wherein the bone cell activating compound is an inorganic phosphate and the bone activating amount is from about 30 mg/kg/day to about 50 mg/kg/day of phosphorous, and not to exceed about 3600 mg P/day.

7. The method of claim 2 wherein the bone cell activating compound is 1,25-dihydroxy vitamin $D_3$ and the bone activating amount is from about 0.001 microgram/kg/day to about 0.03 microgram/kg/day.

8. The method of claim 2 wherein the bone cell activating compound is 25-hydroxy vitamin $D_3$ and the bone activating amount is from about 0.1 microgram/kg/day to about 3 microgram/kg/day.

9. The method of claim 2 wherein the bone cell activating compound is an inorganic fluoride and the bone activating amount is from about 0.1 mg F/kg/day to about 1.0 mg F/kg/day.

10. The method of claim 2 wherein the bone cell activating compound is thyroxine and the bone activating amount is from about 0.01 mg/kg/day to about 0.5 mg/kg/day.

11. The method of claim 2 wherein the bone cell activating compound is triiodothyroxine and the bone activating amount is from about 0.1 microgram/kg/day to about 2.5 microgram/kg/day.

12. The method of calim 2 wherein the bone cell activating compound is prostaglandin $PGE_2$ and the bone activating amount is from about 0.1 mg/kg/day to about 25 mg/kg/day.

13. The method of claim 2 wherein the bone cell activating compound is parathyroid hormone 1-34 and the bone activating amount is from about 0.1 microgram/kg/day to about 3.0 microgram/kg/day administered subcutaneously.

14. The method of claim 1 wherein during the bone resorption inhibition period the ethane-1-hydroxy-1,1-diphosphonic acid, or pharmaceutically-acceptable salt or ester thereof, is administered daily in an amount from about 0.5 mgP/kg/day to about 2.0 mgP/kg/day.

15. The method of claim 4 wherein during the bone resorption inhibition period the ethane-1-hydroxy-1,1-diphosphonic acid, or pharmaceutically-acceptable salt or ester thereof, is administered daily in an amount from about 0.5 mgP/kg/day to about 2.0 mgP/kg/day.

16. A method for treating or preventing osteoporosis in humans comprising administering to a subject afflicted with or at risk to osteoporosis inorganic phosphate and ethane-1-hydroxy-1,1-diphosphonic acid according to a regimen consisting of two or more cycles, whereby each cycle consists of: (a) a bone activating period of about 3 days during which about 30 mg P/kg, in the form of inorganic phosphate, is administered daily to said subject; followed by (b) a bone resorption inhibition period of about 14 days during which said diphosphonic acid, or a pharmaceutically acceptble salt thereof, is administered daily to said subject at a rate of about 1.24 mg P/kg/day followed by (c) a rest period of about 45 days during which the subject received calcium at a rate of from about 500 mg/day to about 1000 mg/day and vitamin D at a rate of about 400 units per day.

* * * * *